United States Patent [19]

Reierson

[11] 4,360,407

[45] Nov. 23, 1982

[54] PROCESS FOR REMOVING GLYCERINE

[75] Inventor: Robert L. Reierson, Midland, Mich.

[73] Assignee: The Dow Chemical Company, Midland, Mich.

[21] Appl. No.: 360,251

[22] Filed: Mar. 22, 1982

[51] Int. Cl.$^3$ ............................ B01D 3/34; C07C 7/20
[52] U.S. Cl. ........................................ 203/34; 203/33; 203/91; 260/462 R; 568/869
[58] Field of Search ................... 203/33, 34, 29, 50, 203/53, 51, 91; 568/869; 260/462 R

[56] References Cited

U.S. PATENT DOCUMENTS

| | | | |
|---|---|---|---|
| 2,345,586 | 4/1944 | Clark | 260/462 R |
| 2,960,447 | 11/1960 | Anderson et al. | 203/34 |
| 3,198,843 | 8/1965 | Barker | 568/869 |
| 3,270,058 | 8/1966 | Sutcliffe | 203/34 |
| 3,806,427 | 4/1974 | Gerrasi et al. | 203/34 |
| 3,914,275 | 10/1975 | Sawyer et al. | 260/462 R |
| 3,947,504 | 3/1976 | Kyo et al. | 260/462 R |

OTHER PUBLICATIONS

Kirk-Othmer Encyclopedia of Chemical Technology, 3rd Edition, vol. 4, Wiley (1978) p. 75.
R. E. Rippere et al., J. Phys. Chem. 47, 204 (1943).
Cotton & Wilkinson, Advanced Inorganic Chemistry, Wiley (1962) pp. 185-186.

*Primary Examiner*—Wilbur L. Bascomb, Jr.
*Attorney, Agent, or Firm*—Douglas N. Deline

[57] ABSTRACT

The distillative separation of a mixture of glycerine and glycerine-based acetal or ketal transesterification products is aided by addition of a borate ester-forming compound to the mixture prior to distillation.

9 Claims, No Drawings

PROCESS FOR REMOVING GLYCERINE

BACKGROUND OF THE INVENTION

The present invention is concerned with an improved distillative process for removing glycerine from organic compounds of nearly equivalent boiling point. More specifically, the invention is concerned with the removal of substantial quantities of glycerine from mixtures comprising glycerine and 4-hydroxymethyl-1,3-dioxanes, 5-hydroxy-1,3-dioxolanes and mixtures thereof.

The preparation of certain 4-hydroxymethyl-1,3-dioxanes and 5-hydroxy-1,3-dioxolanes by reaction under transesterification conditions between glycerine and certain acetals and ketals has been described in U.S. patent application Ser. No. 159,332, filed June 16, 1980, now U.S. Pat. No. 4,320,024. The products formed in the reaction have been found to be usefully employed in various hydraulic fluid formulations. A preferred reaction mixture is formed by the reaction of glycerine and 4,4-dialkoxybutanenitriles, alternatively the same reaction product may be formed by reaction of glycerine directly with the corresponding carbonyl compound, e.g., 4-oxobutanenitrile. For its teaching of the above reaction and the conditions thereof, the above-identified patent application is hereby incorporated by reference.

The presence of glycerine, especially in amounts greater than about 1.0 percent by weight of the acetal and ketal reaction products detrimentally affects the properties of the product particularly in such applications as hydraulic fluids where high wet boiling points of the fluids are adversely affected by the presence of even small amounts of glycerine.

In the above-described transesterification reaction, it has been found that the initial product mixture may contain small amounts of unreacted glycerine. In fact, amounts on a weight basis from about 2 percent to about 10 percent may be present. This glycerine contaminant may be removed by standard techniques of distillation, however, the process has proven particularly tedious and difficult due primarily to the high viscosity of the glycerine component, thereby generally rendering the use of modern packed distillation columns ineffective. As a result, the extended distillation times and elevated temperatures required for the process result in the formation of increased levels of tarry by-products and correspondingly reduced levels of the desired compounds and economic loss.

If an excess of the acetal or ketal reactant is employed in an attempt to drive the reaction to completion and consume the residual glycerine, a significant portion reacts in addition with the free hydroxyl group in the glycerine acetal or ketal reaction product thereby detrimentally forming higher molecular weight non-distilled residues which lower the overall yield.

It would be desirable to provide an improved process for the separative distillation of mixtures comprising glycerine, 4-hydroxymethyl-1,3-dioxanes and 5-hydroxy-1,3-dioxolanes.

SUMMARY OF THE INVENTION

The present invention is an improved process for the distillative separation of glycerine from a mixture comprising glycerine and glycerine-based acetal or ketal derivatives comprising contacting the mixture with a borate ester-forming compound and thereafter distillatively removing the glycerine-based acetal or ketal.

Preferably, the glycerine-based acetal or ketal is a 4-hydroxymethyl-1,3-dioxane, a 5-hydroxy-1,3-dioxolane or a mixture thereof. Most preferably, the compound is a glycerine-based acetal that is the transesterification product of glycerine and 4,4-dimethoxybutanenitrile, especially 4-hydroxymethyl-1,3-dioxolane-2-propanenitrile. According to one of the objects of the present invention it is possible to prepare glycerine acetal or ketal reaction products containing by weight less than about 1.0 percent glycerine.

DETAILED DESCRIPTION OF THE INVENTION

The borate ester-forming compounds for use according to the invention include boric acid as well as salts of boric acid such as alkali metal borates, meta-borates, etc., and hydrates thereof that are soluble in the reaction medium and capable of forming complexes with glycerine at the distillation temperatures employed. Minor pH adjustments to the reaction medium may be employed to accelerate the formation of glycerine adducts. A preferred borate ester-forming compound is boric acid, most preferably in a substantially dehydrated or anhydrous form.

The borate ester-forming compound is added to the reaction mixture in about an equal molar basis or less compared to the glycerine contaminant. While the method in which complexation takes place and the species formed between glycerine and the borate ester-forming compound may differ depending on the borate ester-forming compound, the general principal that is believed to occur may be schematically illustrated as follows for the use of boric acid:

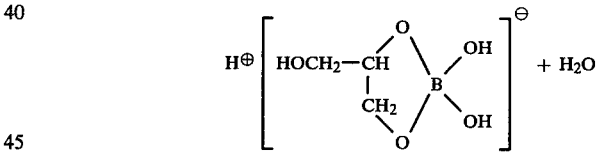

The formation of such polyhydric alcohol complexes has been previously disclosed in Kirk-Othmer, *Encyclopedia of Chemical Technology*, Wiley, 3rd Ed., Vol. 4, p. 67, et seq. (1978).

The unexpected and beneficial advantage of the present process is that despite the presence of additional hydroxyl functionality in the dioxane and dioxolane molecules of the reaction mixture, it appears that the above cyclic borate ester complex of glycerine is preferably formed to the exclusion of other noncyclic borate ester complexes formed from the monohydroxy functional dioxolanes and dioxanes. Additionally, it is a surprising discovery of the invention that the borate ester complexes of glycerine are sufficiently stable that the same do not decompose at the elevated distillation temperatures employed in the process. It has, in fact, been discovered that even at temperatures of about 250° C. or even greater, no decomposition and release of glycerine has been observed.

It is also a surprising discovery of the present invention that the glycerine complexes remain in the distillation residue and are not co-distilled or azeotroped with any of the desired dioxane or dioxolane compounds. It has further been discovered that no detrimental hydrolysis of the dioxane or dioxolane compounds occurs despite the presence of water and an acidic borate ester complex that are believed to be formed by the process.

SPECIFIC EMBODIMENTS

Having described the invention, the following examples are provided as further illustrative and are not to be construed as limiting.

EXAMPLE 1

Glycerine and 4,4-dimethoxybutanenitrile were reacted at elevated temperatures in the presence of p-toluene sulfonic acid. The product mixture obtained comprised 4-hydroxymethyl-1,3-dioxolane-2-propanenitrile and isomers thereof and 4.7 weight percent glycerine. Total product weight was 34.1 g. To this mixture was added 1.13 g of anhydrous boric acid (1:1 molar ratio with glycerine). The solution was warmed to dissolve boric acid. Water was removed under vacuum at 125° C. followed by vacuum distillation. The first fraction obtained, 11.9 g, was analyzed by vapor phase chromatography and found to contain 0.6 percent glycerine and 260 ppm. boron. The second fraction, 8.7 g, was found to contain 0.0 percent glycerine and 34 ppm boron. Boron content of the original solution was calculated at 5760 ppm.

EXAMPLE 2

The reaction conditions of Example b 1 were substantially repeated employing larger amounts of reactants. The initial glycerine content was 6.2 weight percent (2.4 mole) of a 3628 g product mixture. Vacuum distillation at up to 225° C. after addition of 2.4 mole of anhydrous boric acid gave 94 percent yield of the desired glycerine-based acetal products of 4-oxobutanenitrile. Glycerine content was found to be less than 0.1 percent by weight.

What is claimed is:

1. A process for distillatively separating glycerine from a mixture comprising glycerine and glycerine-based acetal or ketal reaction products comprising contacting the mixture with a borate ester-forming compound and thereafter distillatively removing the glycerine-based acetal or ketal reaction products.

2. The process of claim 1 wherein the glycerine-based acetal is a 4-hydroxymethyl-1,3-dioxane, a 5-hydroxy-1,3-dioxolane or a mixture thereof.

3. The process of claim 2 wherein the glycerine-based acetal is the transesterification product of glycerine and 4,4-dimethoxybutanenitrile.

4. The process of claim 3 wherein the glycerine-based acetal is 4-hydroxymethyl-1,3-dioxolane-2-propanenitrile.

5. The process of claim 1 wherein the borate ester-forming compound is boric acid.

6. The process of claim 1 wherein the borate ester-forming compound is anhydrous boric acid.

7. The process of claim 1 wherein the mixture is contacted with an equal molar amount of a borate ester-forming compound based on glycerine.

8. The process of claim 1 wherein the distillation is conducted at a temperature of up to about 250° C.

9. The process of claim 1 wherein the separated glycerine-based acetal or ketal reaction product contains less than about 1.0 percent by weight glycerine.

* * * * *